US00PP28324P3

(12) United States Plant Patent
Suphachadiwong

(10) Patent No.: US PP28,324 P3
(45) Date of Patent: Aug. 22, 2017

(54) *VANDA* PLANT NAMED 'SPCDW1406'

(50) Latin Name: ***Vanda spp.* Jones ex R. Br.**
Varietal Denomination: SPCDW1406

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Bangphra (TH)

( * ) Notice: Subject to any disclaimer, the term of this patent is extended or adjusted under 35 U.S.C. 154(b) by 59 days.

(21) Appl. No.: 14/756,938

(22) Filed: Oct. 30, 2015

(65) Prior Publication Data

US 2016/0143201 P1 May 19, 2016

(30) Foreign Application Priority Data

Nov. 14, 2014 (QZ) ..... PBR 2014/2944

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1406' which is characterized by the combination of a yellow flower with prominent dark brown spotting of both the sepals and petals, a light brown general tonality of the labellum, a light green pedicellate ovary, and the stability of all characteristics from generation to generation. The new variety is a *Vanda*, typically produced as an indoor ornamental plant.

3 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1406'.

CROSS REFERENCE TO RELATED APPLICATIONS

This application claims priority to the Community Plant Variety Rights application number 2014/2944, filed Nov. 14, 2014, which is herein incorporated by reference.

BACKGROUND OF THE INVENTION

Parentage: The *Vanda* variety 'SPCDW1406' is the result of a planned breeding program. The new variety originated as a seedling from the crossing of the unpatented, proprietary seed parent *Vanda* 'A169' with the unpatented, proprietary pollen parent referred to as *Vanda* 'JBP'. The crossing was made by the inventor in his research greenhouse in Chonburi, Thailand in October of 2002.

The new variety was first selected by the inventor, Thumrong Suphachadiwong, a citizen of Thailand, in June of 2007, in a research greenhouse belonging to the inventor in Chonburi, Thailand. After identifying the new variety as a potentially interesting selection, the inventor continued confidential testing and propagation of 'SPCDW1406', assessing stability of the unique characteristics of this variety.

Asexual Reproduction: Asexual reproduction of the new cultivar 'SPCDW1406' was first initiated at a commercial laboratory belonging to the inventor in Chonburi, Thailand by tissue culture in April of 2008, with the first mericlones so reproduced flowering in 2013. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1406' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1406'. These characteristics in combination distinguish 'SPCDW1406' as a new and distinct *Vanda* cultivar:

1. *Vanda* 'SPCDW1406' exhibits a yellow flower; and,
2. *Vanda* 'SPCDW1406' exhibits a prominent dark brown spotting pattern of the sepals and petals; and,
3. *Vanda* 'SPCDW1406' exhibits a light brown general tonality of the labellum; and
4. *Vanda* 'SPCDW1406' exhibits a green general tonality of the pedicellate ovary.

BOTANICAL DESCRIPTION OF THE PLANT

Figure 1:
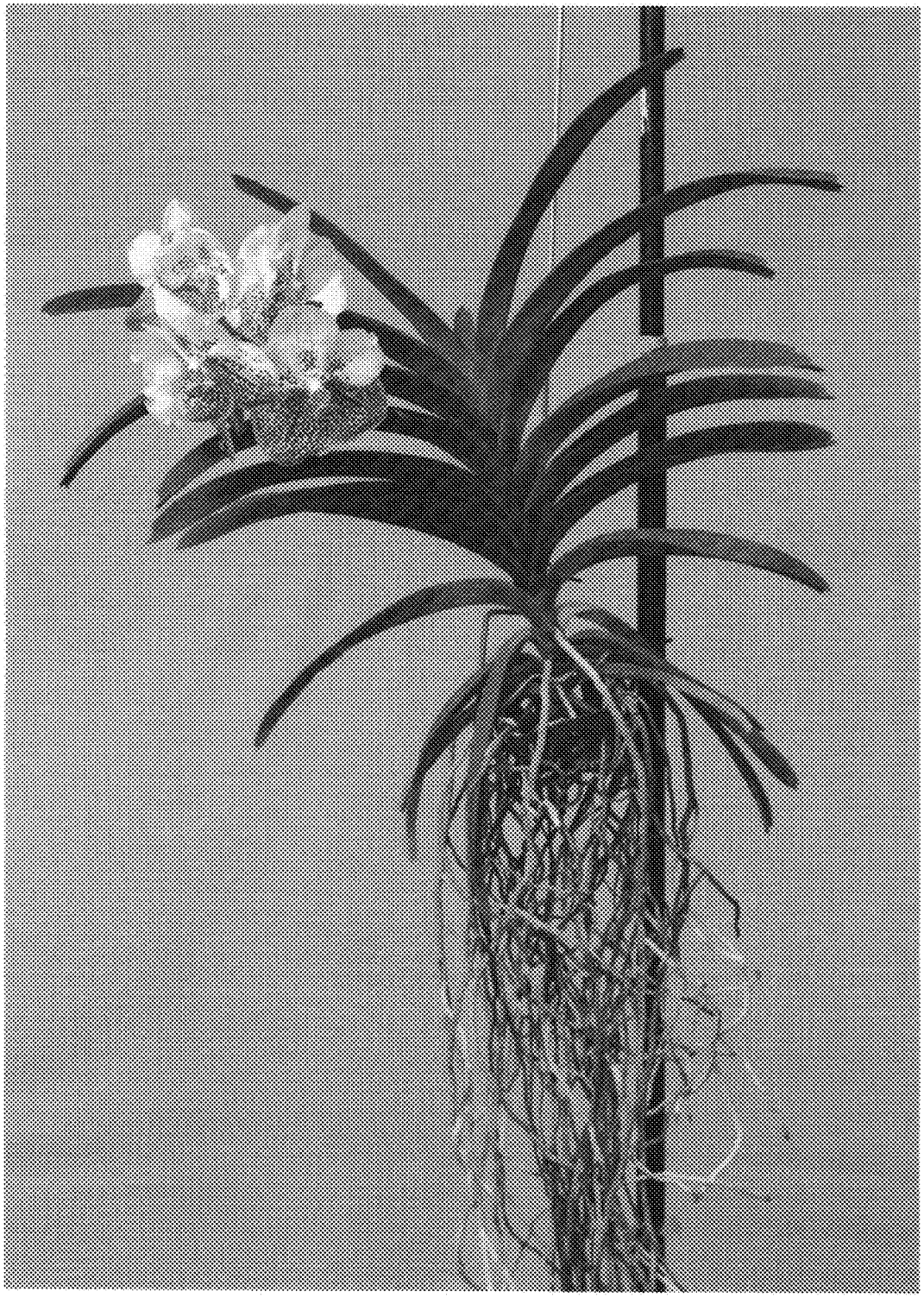
FIG. 1 illustrates, as nearly true as it is reasonably possible to make the same in color photographs of this type, an exemplary plant of 'SPCDW1406' grown in a commercial greenhouse in Honselersdijk, the Netherlands. This plant is approximately 5 years old, shown planted in an 8 by 8 cm container.
Figure 2:
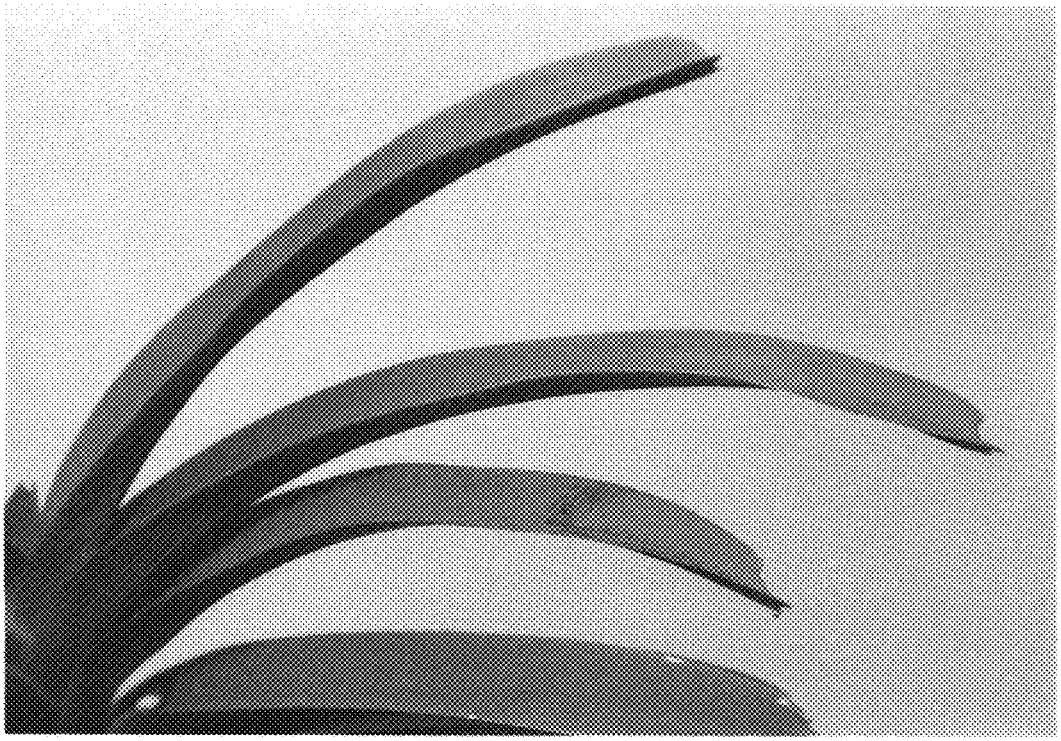
FIG. 2 illustrates, as nearly true as it is reasonably possible to make the same in color photographs of this type, the typical foliage of 'SPCDW1406'.
Figure 3:
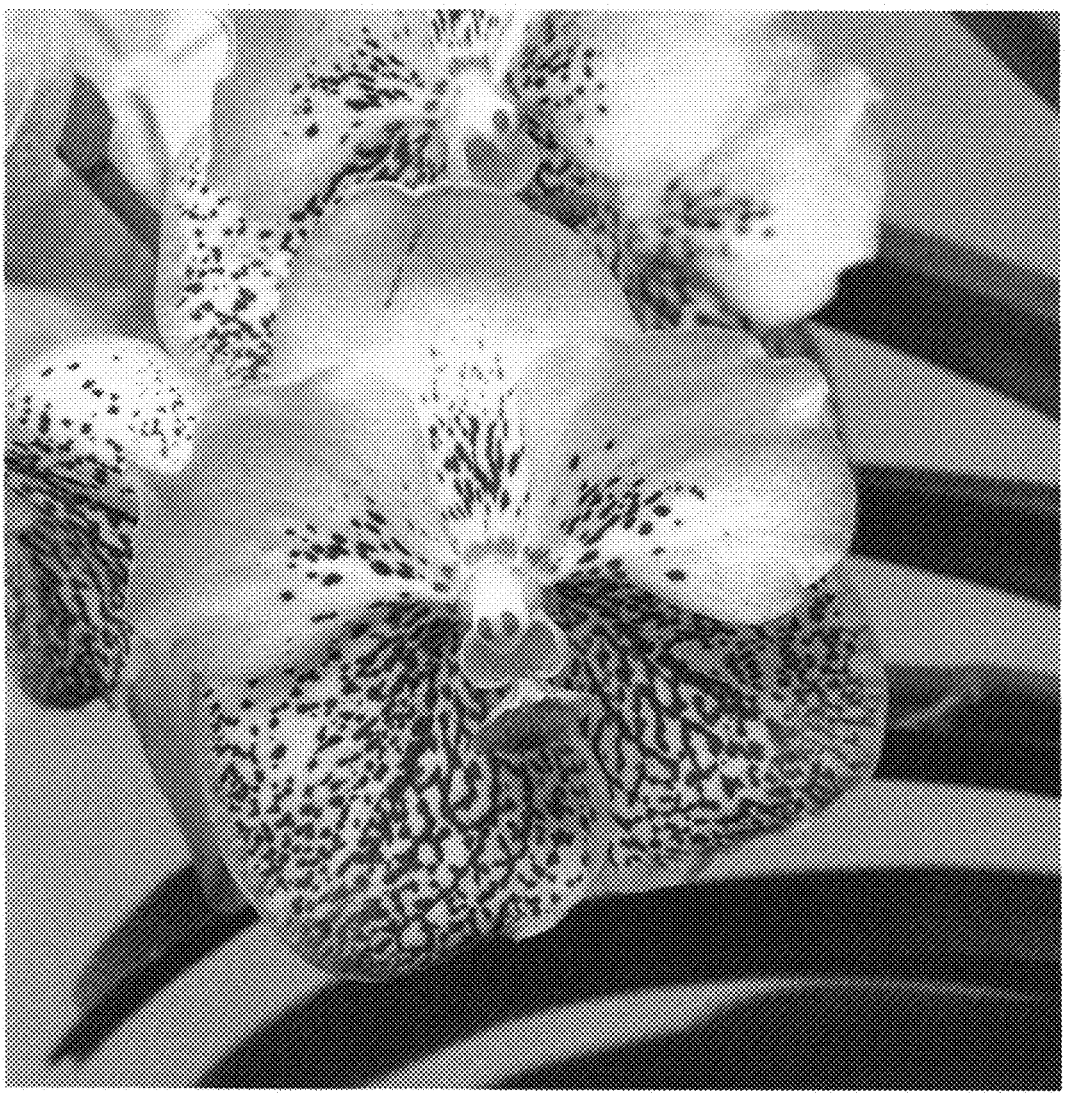
FIG. 3 illustrates, as nearly true as it is reasonably possible to make the same in color photographs of this type, the typical flowers of 'SPCDW1406'.

The following observations and measurements describe a five year-old 'SPCDW1406' plant grown in a greenhouse in Honselersdijk, the Netherlands. Temperatures ranged were approximately 23 degrees Celsius during the day and 19 degrees Celsius at night. No photoperiodic or chemical treatments were given to the plants. When natural lighting fell below 150 Watt, artificial lighting is given at 10,000 lux for 16 hours a day.

Those skilled in the art will appreciate that certain characteristics will vary with older or, conversely, with younger plants. 'SPCDW1406' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'SPCDW1406' and comparisons with other varieties of *Vanda* are provided below.

Plant description:

*Growth habit*.—Monopodial, upright.

*Average height from base (plant grown in hanging basket, so no soil line present) to top of foliage*.—46.4 cm.

*Average height from base (plant grown in hanging basket, so no soil line present) to top of flowers*.—42.2 cm.

*Plant spread*.—Average of 48.4 cm.

*Normal pot size*.—Hanging basket (8 by 8 cm, square).

*Growth rate*.—Moderate.

*Propagation type*.—Meristematic tissue culture propagation using the base of the leaves.

*Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease resistance*.—Good resistance to the normal diseases found in *Vanda*.

*Drought tolerance and cold tolerance*.—Drought tolerance is typical for species. Superior cold tolerance, to approximately 6 degrees Celsius.

Root system:

*General*.—Moderate to heavy rooting with aerial roots only located at the base of the stem, growing from approximately the lowest 35 percent of the stem. Roots very fleshy, non-fibrous. Mature roots becoming woody and inactive.

*Diameter, juvenile roots*.—0.45 cm, on average.

*Dimensions, mature roots*.—59.0 cm long with a diameter of 0.3 cm, on average.

*Color, juvenile roots*.—Greyed-Green, near RHS 192B, with root apices Yellow-Green, near RHS 146B.

*Color, mature roots*.—Yellow-Green RHS 146B.

Foliage:

*Arrangement*.—Distichous.

*Quantity*.—23 leaves, on average.

*Dimensions*.—26.1 cm long and 2.7 cm wide, on average.

*Shape of blade*.—Ligulate; curved downward; strongly carinate.

*Aspect*.—Moderately curved.

*Apex*.—Unequal praemorse.

*Base*.—Sheathing.

*Sheath dimensions*.—1.8 cm long and 1.5 cm wide, on average.

*Sheath color*.—Yellow-Green RHS 144A to 144B.

*Margin*.—Entire.

*Texture of top surface*.—Glabrous, matte.

*Texture of bottom surface*.—Glabrous, matte.

*Color*.—Juvenile foliage, adaxial surface — Green, near RHS 143A. Juvenile foliage, abaxial surface — Green, near RHS 143B. Mature foliage, adaxial surface — Green, nearest to RHS 137A. Mature foliage, abaxial surface — Yellow-Green, between RHS 144A and 146A.

*Venation*.—Parallel.

*Venation coloration*.—Not distinguishable from the leaf surface; coloration is the same as surrounding leaf.

*Petiole*.—No petioles present, leaves sessile.

Inflorescence:

*Flowers per stem*.—Average of 10.

*Inflorescence arrangement*.—Axially placed raceme.

*Inflorescence height*.—Approximately 17.1 cm (measured from base of lowest flower to top of upper flower).

*Inflorescence width*.—Approximately 15.5 cm.

*Peduncle*.—Length — Approximately 26.0 cm. Width — Approximately 0.5 cm. Aspect — Approximately 35° angle to rosette. Strength — Strong. Texture — Glabrous and very slightly glossy. Color — Yellow-Green, near RHS 144A.

Bud:

*Rate of opening*.—Buds open approximately three weeks from first sight.

*Length*.—Average of 1.8 cm.

*Diameter*.—Average of 1.8 cm.

*Shape*.—Broad obovate to near globose.

*Color*.—Yellow, near RHS 3D.

Flower:

*Flower type*.—Zygomorphic (orchidaceous), typical shape for the genus *Vanda*.

*Shape*.—Zygomorphic, consisting of three sepals and three petals, one of which is transformed into a labellum; the two lateral petals heavily overlap the dorsal sepal and the lateral sepals; lateral sepals moderately overlap one another and also the dorsal sepal.

*Length (height)*.—Approximately 10.0 cm.

*Width*.—Approximately 8.5 cm.

*Depth*.—Approximately 2.5 cm.

*Fragrance*.—No fragrance.

*Persistent*.—No.

*Quantity of petals*.—3; two conventional petals and one labellum.

*Petals*.—Arrangement — One lateral petal on each side. Length — Approximately 4.4 cm. Width — Approximately 4.4 cm. Shape — Broad ovate to near orbicular. Apex — Obtuse. Base — Cuneate. Margin — Entire; undulate. Texture of upper forward surface — Glabrous, matte, velvety. Texture of lower back surface — Glabrous, matte, velvety. Color when opening, forward surface — Yellow, near RHS 4D, and darker near the margins and apex, near RHS 3D to 4C; tinged with Greyed-Yellow RHS 161D near the apex; dotted with Red-Purple RHS 59A at the base. Color when opening, back surface — Yellow, near RHS 4C and 4D, and tinged with Greyed-Yellow RHS 161D near the margins and apex. Color when fully opened, forward surface — Yellow, near RHS 5D, and darker at the margins, near RHS 6D; tinged with Greyed-Yellow RHS 161D near the apex; dotted at the base with Greyed-Purple RHS 183A. Color when fully opened, back surface — Yellow, near RHS 6D, and tinged with Greyed-Yellow RHS 162C at and near the margins and apex. Fading, forward surface — Not fading. Fading, back surface — Not fading. Venation — Not visible. Venation color, fully opened, forward surface — Not distinguishable from the petal; coloration is the same as surrounding petal. Venation color, fully opened, back surface — Not distinguishable from the petal; coloration is the same as surrounding petal.

*Labellum*.—Shape — Three-lobed; the shape of the lateral lobes is near orbicular, and the aspect is strongly concave; the central lobe is undeeply emarginated and therefor irregularly shaped; the aspect of the central lobe is strongly concave. Length — Overall length — Approximately 1.7 cm. Central lobe — Approximately 1.7 cm. Lateral lobes — Approximately 0.6 cm. Width — Overall width — Approximately 1.5 cm. Central lobe — Approximately 1.5 cm. Lateral lobes — Approximately 0.7 cm. Apex — Central lobe — Emarginate. Lateral lobes — Obtuse. Base — Central lobe — Cuneate. Lateral lobes — Cuneate. Margin — Central lobe — Entire; slightly undulated. Lateral lobes — Entire; moderately undulated. Texture and luster of upper surface — Central lobe — Glabrous and slightly glossy. Lateral lobes — Glabrous and slightly glossy. Texture and luster of lower surface — Central lobe — Glabrous and matte. Lateral lobes — Glabrous and matte. Color when opening, forward surface — Central lobe — Greyed-Orange, near RHS 175A; base is Yellow-Green, near 154D. Callosities are the same color as the surface. Lateral lobes — Yellow-Green, near RHS 154B; finely dotted at the base with Greyed-Purple, near RHS 183B. Color when opening, back surface — Central lobe — Yellow-Green, near RHS 154C to 154D; margins and apex are Greyed-Orange, near RHS 177B; finely dotted at the base with Greyed-Purple, near RHS 183D. Lateral lobes — Yellow-Green, near RHS 154C. Color when fully opened, forward surface — Central lobe — Greyed-Orange, near RHS 175A; base is Yellow-Green, near 154D. Callosities are the same color as the surface. Lateral lobes — Yellow-Green, near RHS 154B; finely dotted at the base with Greyed-Purple, near RHS 183B. Color when fully opened, back surface — Central lobe — Yellow-Green, near RHS 154C to 154D; margins and apex are Greyed-Orange, near RHS 177B; finely dotted at the base with Greyed-Purple, near RHS 183D. Lateral lobes — Yellow-Green, near RHS 154C. Fading, forward surface — Not fading. Fading, back surface — Not fading. Venation color, fully opened, forward surface — No venation visible on labellum. Venation color, fully opened, back surface — No venation visible on labellum.

*Spurs*.—Quantity — Average of 1. Appearance — Short triangular, in line with central lobe of labellum. Length — Approximately 0.7 cm. Width — Approximately 0.3 cm. Height — Approximately 0.6 cm, at the base. Shape — Short triangular. Apex — Obtuse. Base — Broad Cuneate. Margin — Entire. Texture — Glabrous, matte. Color — Yellow, near RHS 4C.

*Sepals*.—Quantity — Average of 3. Appearance — One dorsal sepal (pointing upright) and two lateral sepals. Length — Dorsal sepal — Approximately 4.9 cm. Lateral sepals — Approximately 5.2 cm. Width — Dorsal sepal — Approximately 4.3 cm. Lateral sepals — Approximately 5.2 cm. Shape — Dorsal sepal is broad ovate and lateral sepals are broad ovate to reniform. Apex — Obtuse. Base — Cuneate. Margin — Entire. Texture — Glabrous, matte, velvety. Color, when opening and when fully opened — Dorsal sepal, upper side — Yellow, near RHS 3D, and slightly darker at the margins, near RHS 6D; tinged with Greyed-Orange RHS 163B near the apex; dotted with Greyed-Purple RHS 183A at the base, with a Greyed-Orange RHS N167A radial band at the base (attachment to column). Dorsal sepal, under side — Yellow, near RHS 5D; tinged with Greyed-Yellow, in between RHS 162B and 162C, at and near the margins and apex. Lateral sepal, upper side — Yellow, near RHS 3C; tinged with Greyed-Yellow RHS 161B at and near the margins and apex; heavily dotted with Greyed-Purple, near RHS183A. Lateral sepal, under side — Near Green-Yellow, nearest to a combination of RHS 1C and Yellow 5C; tinged Greyed-Yellow at and near the margins and apex, near RHS 162A. Venation color, fully opened, forward surface — Not distinguishable from the sepal; coloration is the same as surrounding sepal. Venation color, fully opened, back surface — Main vein is Yellow-Green, near RHS 151D; all other veins are not visible.

*Pedicels*.—Length — Approximately 5.2 cm. Diameter — Approximately 0.4 cm. Angle — Approximately 65° angle to peduncle. Strength — Very strong. Texture — Glabrous, axially angled with 5 "ribs", axially twisted (due to resupination), glossy. Color — Yellow-green, near RHS 150D, and darker near proximal end, near RHS 1508 to 150C; Yellow intonations near RHS 154C to 154D are visible toward the distal end.

Reproductive organs: Stamens, style and stigma fused into column? Yes.

*Column length*.—Approximately 0.7 cm.

*Column diameter*.—Approximately 0.65 cm.

*Column color*.—Yellow-Green, in between RHS 150C and 150D.

*Ovary position*.—Inferior.

*Ovary diameter*.—Approximately 0.6 cm.

*Ovary color*.—Yellow, near RHS 2D; top (cover of pollinia) with two dots, near RHS 200D.

*Pollinia color*.—Yellow, near RHS 13A.

Seed and fruit: No fruit and seed production has been detected to date.

COMPARISONS WITH THE PARENT PLANTS

Plants of the new cultivar 'SPCDW1406' are similar to the seed parent, *Vanda* 'A169', in most horticultural characteristics. However 'SPCDW1406' differs from the seed parent in the following characteristics:

1. 'SPCDW1406' exhibits a yellow general tonality of the flower, whereas 'A1691' exhibits a greyed-yellow general tonality of the flower.
2. The flowers of 'SPCDW1406' are larger than those of 'A169'.

Plants of the new cultivar 'SPCDW1406' are similar to the pollen parent, *Vanda* 'JBP', in most horticultural characteristics. However 'SPCDW1406' differs from the pollen parent in the following characteristics:

1. 'SPCDW1406' exhibits a yellow general tonality of the flower with a prominent dark brown spotting pattern, whereas the flowers of 'JBP' exhibit a light cream-yellow color of the upper portion of the perianth and a greyed-yellow color of the lower portion of the perianth, with a light brown spotting pattern.
2. The flowers of 'SPCDW1406' exhibit a dark brown spotting pattern, whereas the flowers of 'JBP' exhibit a lighter brown spotting pattern.
3. The inflorescence of 'SPCDW1406' are significantly shorter than those of 'JBP'.

COMPARISONS WITH SIMILAR *VANDA* CULTIVARS KNOWN TO THE INVENTOR

'SPCDW1406' is similar in many horticultural characteristics to the commercial variety *Vanda* 'SPCDW1403' (U.S. Plant patent application Ser. No. 14/756,773). However 'SPCDW1406' differs from 'SPCDW1403' in the following characteristics:

1. 'SPCDW1406' exhibits a yellow general tonality of the flower, whereas 'SPCDW1403' exhibits a greyed-yellow general tonality of the flower.
2. The flowers of 'SPCDW1406' exhibit a prominent dark brown spotting pattern, whereas the flowers of 'SPCDW1403' exhibit a lighter brown spotting pattern.
3. 'SPCDW1406' exhibits a light brown general tonality of the labellum, whereas 'SPCDW1403' exhibits a light green general tonality of the labellum.
4. The pedicellate ovary of 'SPCDW1406' exhibits a lighter green general tonality when compared to the general tonality of the ovary of 'SPCDW1403' which is a darker green.

That which is claimed is:

1. A new and distinct variety of *Vanda* plant named 'SPCDW1406', substantially as described and illustrated herein.

* * * * *